(12) United States Patent
Athanikar

(10) Patent No.: US 6,372,784 B1
(45) Date of Patent: Apr. 16, 2002

US006372784B1

(54) BISMUTH-CONTAINING COMPOUNDS IN TOPICAL DOSAGE FORMS FOR TREATMENT OF CORNEAL AND DERMAL WOUNDS

(75) Inventor: Narayan K. Athanikar, Irvine, CA (US)

(73) Assignee: Josman Laboratories, Inc., Orange, CA (US)

( * ) Notice: Subject to any disclaimer, the term of this patent is extended or adjusted under 35 U.S.C. 154(b) by 0 days.

(21) Appl. No.: 09/524,891

(22) Filed: Mar. 14, 2000

Related U.S. Application Data

(63) Continuation of application No. 09/253,559, filed on Feb. 19, 1999, now abandoned, which is a continuation of application No. 08/918,322, filed on Aug. 26, 1997, now abandoned, which is a continuation-in-part of application No. 08/518,971, filed on Aug. 24, 1995, now abandoned, which is a continuation-in-part of application No. 08/385,060, filed on Feb. 7, 1995, now abandoned.

(51) Int. Cl.[7] ......................... A61K 31/29; A61K 33/24; A01N 59/16

(52) U.S. Cl. ......................................... 514/503; 424/653
(58) Field of Search ............................... 424/400, 653; 514/503

(56) References Cited

U.S. PATENT DOCUMENTS

| | | |
|---|---|---|
| 3,011,949 A | 12/1961 | Bilotti |
| 3,247,051 A | 4/1966 | Leebrick |
| 3,352,689 A | 11/1967 | Bilotti |
| 3,577,533 A | 5/1971 | Rider |
| 3,651,208 A | 3/1972 | Lauster |
| 3,824,006 A | 7/1974 | Voit |
| 3,929,449 A | 12/1975 | Hedrich |
| 3,943,258 A | 3/1976 | Bahoshy et al. |
| 3,973,041 A | 8/1976 | DuRoss |
| 3,982,023 A | 9/1976 | Bahoshy et al. |
| 4,016,268 A | 4/1977 | Goldenberg et al. |
| 4,055,655 A | 10/1977 | Maurer et al. |
| 4,118,480 A | 10/1978 | Williams |
| 4,153,685 A | 5/1979 | Serfontein |
| 4,180,473 A | 12/1979 | Maurer et al. |
| 4,208,431 A | 6/1980 | Friello et al. |
| 4,217,368 A | 8/1980 | Witzel et al. |
| 4,514,421 A | 4/1985 | Herschler |
| 4,652,444 A | 3/1987 | Maurer |
| 4,670,245 A | 6/1987 | Vasquez et al. |
| 4,680,309 A | 7/1987 | Maurer |
| 4,800,083 A | 1/1989 | Hom et al. |
| 4,801,454 A | 1/1989 | Coveney |
| 4,801,608 A | 1/1989 | Bos et al. |
| 4,822,597 A | 4/1989 | Faust et al. |
| 4,879,116 A * | 11/1989 | Fox et al. ................... 424/682 |
| 4,917,899 A | 4/1990 | Geoghegan et al. |
| 4,940,695 A | 7/1990 | Coveney et al. |
| 4,956,386 A | 9/1990 | McLoughlin et al. |
| 4,965,382 A | 10/1990 | Furlan |
| 4,975,270 A | 12/1990 | Kehoe |
| 5,002,776 A | 3/1991 | Geoghegan et al. |
| 5,013,560 A | 5/1991 | Stentz et al. |
| 5,017,367 A * | 5/1991 | Stojkoski ................... 424/63 |
| 5,093,342 A | 3/1992 | Tomoi et al. |
| 5,192,752 A | 3/1993 | Chapura et al. |
| 5,196,205 A | 3/1993 | Borody |
| 5,256,684 A | 10/1993 | Marshall |
| 5,260,304 A | 11/1993 | Gergely et al. |
| 5,264,222 A | 11/1993 | Groenendaal et al. |
| 5,286,492 A | 2/1994 | Dettmar |
| 5,286,497 A | 2/1994 | Hendrickson et al. |
| 5,294,433 A | 3/1994 | Singer et al. |
| 5,304,540 A | 4/1994 | Blackburn et al. |
| 5,324,750 A | 6/1994 | Lincoln et al. |
| 5,334,582 A | 8/1994 | Blackburn et al. |
| 5,352,679 A | 10/1994 | Ferrieri et al. |
| 5,368,845 A | 11/1994 | Gaffar et al. |
| 5,372,815 A | 12/1994 | Hodutu |
| 5,385,739 A | 1/1995 | Debregeas et al. |
| 5,403,830 A | 4/1995 | Place |
| 5,425,948 A | 6/1995 | Olivieri |
| 5,466,681 A | 11/1995 | Krivan et al. |
| 5,476,669 A | 12/1995 | Borody |
| 5,514,660 A | 5/1996 | Zopf et al. |
| 5,536,510 A | 7/1996 | Tyrpin et al. |
| 5,559,096 A | 9/1996 | Edwards et al. |
| 5,601,848 A | 2/1997 | Marshall |
| 5,604,212 A | 2/1997 | Blank |

(List continued on next page.)

FOREIGN PATENT DOCUMENTS

| | | |
|---|---|---|
| AU | 262452 | 3/1963 |
| AU | 65846 | 5/1967 |
| DE | 1963496 | 6/1971 |
| DE | 2012187 | 9/1971 |
| EP | 0206627 B1 | 12/1968 |
| EP | 0075992 A1 | 4/1983 |
| EP | 0206626 A2 | 12/1986 |
| EP | 0403048 A2 | 6/1989 |
| EP | 0367484 A1 | 5/1990 |
| EP | 0375063 A1 | 6/1990 |

(List continued on next page.)

OTHER PUBLICATIONS

Abstracts of Papers *Gastroenterology*, 1986, vol. 88, No. 5, part 2, pp. 1434, 1585, 1599, 1620.*
Abstracts of Papers *Gastroenterology*, vol. 90, No. 5, Part 2, p. 1580.*

(List continued on next page.)

*Primary Examiner*—Alton Pryor
(74) *Attorney, Agent, or Firm*—Brinks Hofer Gilson & Lione

(57) ABSTRACT

This invention provides for a method for treatment of corneal and dermal wounds by administering bismuth compounds in topical dosage forms. Bismuth compounds cause stimulation of release of growth factors in damaged tissue to promote regeneration of epithelial cells and hence accelerate wound healing. These bismuth compounds also have good antimicrobial activity against several anaerobic bacteria involved in diaper rash exacerbation.

15 Claims, 2 Drawing Sheets

U.S. PATENT DOCUMENTS

| | | | |
|---|---|---|---|
| 5,788,974 A | 8/1998 | D'Amico et al. | |
| 5,804,549 A | 9/1998 | Blackburn et al. | |
| 5,834,002 A | 11/1998 | Athanikar | |
| 5,840,281 A | 11/1998 | Gaffar et al. | |

FOREIGN PATENT DOCUMENTS

| | | |
|---|---|---|
| EP | 0377477 A1 | 7/1990 |
| EP | 0437294 A1 | 7/1991 |
| FR | 070408 | 3/1968 |
| FR | 102365 | 7/1968 |
| FR | 121072 | 12/1968 |
| GB | 1144915 | 3/1964 |
| GB | 1107655 | 3/1968 |
| GB | 1478742 | 7/1977 |
| GB | 2 195 248 | 4/1988 |
| GB | 2195890 A | 4/1988 |
| GB | 2195891 A | 4/1988 |
| GB | 2195892 A | 4/1988 |
| JP | 8-20543 | 1/1996 |
| WO | WO86/05981 | 10/1986 |
| WO | WO91/03241 | 3/1991 |
| WO | WO92/01457 | 2/1992 |
| WO | WO 97/00668 | 1/1997 |

Abstracts of Papers, *Gastroenterology,* vol. 92, No. 5, Part 2, p. 1518.*

"Aldefur" *Unlisted Drugs* (Nov. 1970) vol. 22, No. 11, p. 163b.*

"Corygest" *Unlisted Drugs* (Mar. 1982) vol. 34, No. 3, pp. 38.*

"Uplex 59051B" *Rote List* (1978).*

1994 Annual Report for Applied Microbiology, Inc.; distributed with notice of Annual Shareholders Meeting which was mailed Feb. 1995.*

Abraham et al. "*Helicobacter pylori* in its lair: a role in ulcer recurrence?" *Indian Journal of Gastroenterology* (1990) vol. 9, No. 4, pp. 265–269.*

Andersen et al. "*Campylobacter pylori* in Peptic Ulcer Disease. II. Endoscopic Findings and Cultivation of *C. pylori."* Scand. J. Gastroenterol. (1988), pp. 760–764.*

Axon "[chapter] V. Helicobacter pylori therapy: Effect on peptic ulcer disease" *Journal of Gastroenterology and Hepatology* (1991) vol. 6, pp. 131–137.*

Axon "*Campylobacter pylori*—Therapy Review" *Scand. J. Gastroenterol.,* (1989) vol. 24, supp. 160, pp. 35–38.*

Bader. "The Safety Profile of De–Nol®" *Digestion,* vol. 37, supp. 2 (1987) pp. 53–59.*

Beil et al. "Studies on the Mechanism of Action of Colloidal Bismuth Subcitrate" *Pharmacology,* (1993) vol. 47, pp. 135–144.*

Benet "Safety and Pharmacokinetics: Colloidal Bismuth Subcitrate", *Scand. J. Gastroenterol* (1989) vol. 26, supp. 185, pp. 29–35.*

Bettarello "Anti–ulcer therapy. Past to present" *Digestive Diseases and Sciences* (Nov. 1985) vol. 30, supp. 11, pp. 36S–42S.*

Bianchi Porro et al. "Comparison of tripotassium dicitrato bismuthate (TDB) tablets and ranitidine in healing and relapse of duodenal ulcers" *The British Society of Gastroenterology* (1984) vol. 25, p. A565, No. F51 [abstract only].

Bianchi Porro et al. "Maintenance therapy with colloidal bismuth subcitrate in duodenal ulcer disease" *Digestion* (1987) vol. 37, supp. 2, pp. 47–52.

Bianchi Porro et al. "Relapse Rates in Duodenal Ulcer Patients Formerly Treated with Bismuth Subcitrate or Maintained with Cimetidine" *The Lancet* (1984) vol. 2, p. 698.

Blaser et al. "Campylobacter Enteritis" *New England Journal of Medicine* (1981) vol. 305, pp. 1444–1452.

Bornkessel "*Helicobacter pylori* bei Ulkuserkrankungen" *Arneimitteltherapiel* (13.Jahrgang/Heft1/1995) pp. 17–19 [in German].

Borody et al. "High Efficacy, Low Dose Triple Therapy (TT) for *Helicobacter pylori (HP)*" *Gastroenterology* (1992) vol. 102, No. 4, part 2, p. A44 [abstract only].

Börsch et al. "*Helicobacter pylori"* Pharmacology of peptic ulcer disease (1991) pp. 106–147.

Bosy et al. "Relationship of Oral Malodor to Periodontitis: Evidence of independence in discrete subpopulations" *J. Periodontol* (1992) vol. 65, No. 1 pp. 37–46.

Bouvet "Bismuth salts used in gastro–enterology. Data of animal investigations" *Ann. Pharm. Fr* (1980), vol. 38, pp. 447–454 [in French with English summary].

Boyd et al. "Recurrent ulcer disease" *Gastroenterology Clinics of America. Helicobacter pylori Infection* (Mar. 1993) vol. 22, No. 1, pp. 14–42.

Breuer et al. "Epidemiologie und Pathogenese der *Helicobacter pylori*–infektion" *Gastro–Ligo Report* (Mar./Apr. 1994) pp. 1–5 [in German].

Brogden et al. "Tri–potassium di–citrato bismuthate: a report of its pharmacological properties and therapeutic efficacy in peptic ulcer" *Drugs* (1976) vol. 12, pp. 401–411.

Chemical Abstract Service (1983) vol. 98, p. 384, No. 221850c [abstract only].

Coghill et al. "The ultrastructural localization of De–Nol (colloidal tripotassium dicitrato–bismuthate–TDB) in the upper gastrointestinal tract of man and rodents following oral and instrumental administration" *Chemical Abstracts Service* (1983) vol. 98, p. 15, No. 172475y [abstract only].

Colson "The treatment of chronic colitis and colopathies by a new association of bismuth, mucilage, oxyquinoline and meprobamate" *Revue des corps de santé des Armées* (1966) vol. 7, No. 2, p. 319–334 [English translation of the French article].

Correa et al. "*Helicobacter pylori* and gastric cancer" *Helicobacter pylori and gastroduodenal disease* (1992) pp. 157–164.

De Boever et al. "Assessing the Contribution of Anaerobic Microflora of the Tongue to Oral Malodor" *JADA,* (Oct. 1995) vol. 126, pp. 1384–1393.

Deák et al. "A controlled clinical trial with De–Nol (tripotassium dicitrato bismuthate) in patients with gastric ulcer" *Int J. Tissue Reac* (1983) vol. 5, No. 4, pp. 397–401.

Desai et al. "Dental Plaque: A Permanent Reservoir of *Helicobacter pylori?" Scand. J. Gastroenterol* (1991) vol. 26, pp. 1205–1208.

Dixon "[chapter] IV. *Helicobacter pylori* and peptic ulceration: histopathological aspects" *Journal of Gastroenterology and Hepatology* (1991) vol. 6, pp. 125–130.

Dobrilla et al. ."Influence of ulcer healing agents on ulcer relapse after discontinuation of acute treatment: a pooled estimate of controlled clinical trials" *Gut* (1988) vol. 29, pp. 181–187.

Dunn "The role of *Helicobacter pylori* in gastrointestinal diseases" *Gastrointestinal Disease Management* (Aug. 1991), pp. 173–182.

Eberhardt et al. "Effect of oral bismuthsubsalicylate on Campylobacter pyloridis and on duodenal ulcer" *Gastroenterology* (May 1987) vol. 92, No. 5, p. 1379 [abstract only].

Eidt et al. "The significance of *Helicobacter pylori* in relation to gastric cancer and lymphoma" *European Journal of Gastroenterology & Hepatology* (1995) vol. 7, No. 4, pp. 318–321.

Forman et al. "An international association between *Helicobacter pylori* infection and gastric cancer" *The Lancet* (May 29, 1993) vol. 341, No. 8857, pp. 1359–1362.

Forman et al. "*H. pylori* and gastric cancer: the significance of the problem" *Helicobacter pylori Basic Mechanisms to Clinical Cure.* (1994), pp. 461–468.

Freedberg et al. "The Presence of Spirochetes in Human Gastric Mucosa" *American Journal of Digestive Diseases* (1940) vol. 7, pp. 443–445.

Gisselbrecht et al. "Treatment of constipation and colitis by the association of bismuth subnitrate and Karaya gum" *Lyon Med.,* (1970) vol. 223, No. 18, pp. 951–958 [French article and English translation].

Goh et al. "*Helicobacter pylori* Infection and Non–Ulcer Dyspepsia: The Effect of Treatment with Colloidal Bismuth Subcitrate", *Scand. J. Gastroenterol* (1991) vol. 26, pp. 1123–1131.

Goodman. *The Pharmacological Basis of Therapeutics.* Fifth edition. (1975) pp. 930, 997–998.

Goodwin "Taxonomy of *Helicobacter pylori* and related bacteria" *Helicobacter pylori, gastritis and peptic ulcer* (1990) pp. 1–8.

Goodwin et al. "The minimum inhibitory and bactericidal concentrations of antibiotics and anti–ulcer agents against Campylobacter pyloridis" *J. Antimicrobial Chemotherapy* (1986) vol. 17, pp. 309–314.

Gorbach "Bismuth therapy in gastrointestinal diseases" *Gastroenterology* (Sep. 1990) vol. 99, No. 3, pp. 863–875.

Graham "*Helicobacter pylori:* human pathogen or simply an opportunist?" *The Lancet* (Apr. 29, 1995) vol. 345, pp. 1095–1097.

Graham et al. "Factors influencing the eradication of *Helicobacter pylori* with triple therapy" *Gastroenterology* (1992) vol. 102, pp. 493–496.

Hamilton et al. "Effects of tripotassium dicitrato–bismuthate (TDB) tablets or cimetidine in the treatment of duodenal ulcer" *Gut* (Dec. 1983) vol. 24, No. 12, pp. 1148–1151.

Héraud et al. "Therapeutical trial of an association of an insoluble bismuth salt and a Karaya gum in gastro–intestinal pathology" *Lille Medical, 3rd Series,* (1969) vol. XIV, No. 6, supplement, pp. 677–679 [French article with English translation].

Hislop et al. "Histological Improvement of Active Chronic Gastritis in Patients Treated with De–Nol", presented at a meeting of the Gastroenterological Society of Australia (Mar. 11–14, 1984), *Gastroenterological Society of Australia* (Dec. 1984) p. 907 [abstract only].

Hosking et al. "Duodenal Ulcer Healing by Eradication of *Helicobacter pylori* without anti–acid treatment: randomised controlled trials" *The Lancet* (1994) vol. 343, pp. 508–510.

Jensen et al. "Chewing gum and lozenges as delivery systems for noscapine" *Acta Pharm. Nord* (1991) vol. 3, No. 4, pp. 219–222.

Jones et al. "Acid suppression in duodenal ulcer: a meta–analysis to define optical dosing with antisecretory drugs" *Gut* (1987), vol. 28, pp. 1120–1127.

Kleinberg et al. "Salivary and Metabolic factors involved in oral malodor formation" *J. Peridontol* (1992) vol. 63, No. 9, pp. 768–775.

Konturek et al. "Advances in the understanding of the mechanism of cytoprotective action by colloidal bismuth subcitrate" *Scand. J. Gastroenterol* (1986) vol. 21, supp. 122, pp. 6–10.

Konturek et al. "Studies on the gastroprotective and ulcer –healing effects of colloidal bismuth subcitrate" *Digestion* (1987) vol. 37, supp. 2, pp. 8–15.

Koo et al. "Selective Coating of Gastric Ulcer by Tripotassium Dicitrato Bismuthate in the Rat", *Gastroenterology* (May 1982) vol. 83, No. 5 pp. 864–870.

Lambert, I. *The Lancet* (Apr. 10, 1993) vol. 341, p. 957 [letter only].

Lambert, J.R. "Clinical Indications and Efficacy of Colloidal Bismuth Subcitrate" *Scand. J. Gastroenterol* (1991) vol. 26, suppl. 185, pp. 13–21.

Lambert, J.R. et al. "*Helicobacter pylori*" *Mechanisms of Injury, Protection and Repair of the Upper Gastrointestinal Tract* (1991), p. 19–28.

Lambert, T. et al. "Susceptibility of Campylobacter pyloridis to 20 Antimicrobial Agents" *Antimicrobial Agents and Chemotherapy* (Sep. 1986) vol. 30, No. 3, pp. 510–511.

Lane et al. "Tripotassium dicitrato–bismuthate tablets v liquid in the treatment of duodenal ulcers" *N Z Med J* (Mar. 27, 1985) vol. 98, No. 775, pp. 191–192.

Langenberg et al. "Campylobacter–like Organisms in the Stomach of Patients and Healthy Individuals" *The Lancet* (Jun. 16, 1984) vol. 1 pp. 1348–1349; 1336–1337.

Lashner et al. "Testing Nicotine Gum for Ulcerative Colitis Patients" *Digestive Diseases and Sciences* (Jul. 1990), vol. 35, No. 7, pp. 827–832.

Lee, F.I. et al. "Comparison of Tri–potassium Di–citrato Bismuthate Tablets with Ranitidine in Healing and Relapse of Duodenal Ulcers" *The Lancet* (Jun. 8, 1985) vol. 1, pp. 1299–1301.

Lee, S.P. "The Mode of Action of Colloidal Bismuth Subcitrate" *Scand. J. Gastroenterol* (1991) vol. 26, supp. 1985, pp. 1–6.

Lee, S.P. et al. "Increased healing of gastric and duodenal ulcers in a controlled trial using tripotassium dicitrato–bismuthate" *Med J. Aust* (May 28, 1977) vol. 1, No. 22, pp. 808–812.

Lees et al. "A freeze–injured skin graft model for the quantitative study of basic fibroblast growth factor and other promoters of angiogenesis in wound healing" *British Journal of Plastic Surgery* (1994) vol. 47, pp. 349–359.

Logan et al. "One week eradication regimen for *helicobacter pylori*" *The Lancet* (1991) vol. 338, pp. 1249–1252.

Lorber "Antipeptic agents, carbenoxolone, and mucosal coating agents: status report" *Chemical Abstracts Service* (1981) vol. 94, No. 93, No. 168025b [abstract only].

Marcheggiano et al. "Campylobacter–Like Organisms (CLOs) Gastritis and Peptic Ulcer", (1986) p. 1533, [abstract only].

Marshall "*Helicobacter pylori*" *The American Journal of Gastroenterology* (1994) vol. 89, No. 8, pp. S116–S128.

Marshall "Treatment strategies for *Helicobacter pylori* infection" *Gastroenterology Clinics of America. Helicobacter pylori infection.* vol. 22, No. 1, pp. 186–195.

Marshall et al. "Histological improvement of Active Chronic Gastritis in Patients Treated with De–Nol" *Australia & New Zealand J. of Medicine* (Dec. 1984) vol. 14, p. 907.

Marshall et al. "Pyloric Campylobacter Infection and Gastroduodenal Disease" *The Medical Journal of Australia* (Apr. 15, 1985) vol. 142, pp. 439–444.

Marshall et al. "Pyloric Cambylobacter Serology" *The Lancet* (Aug. 4, 1984) vol. 2, p. 281 [letter only].

Marshall et al. "Spiral bacteria in the human stomach: a common finding in patients with gastritis and duodenal ulcer" *Campylobacter II*, Proceedings of the Second International Workshop on Campylobacter Infections (1983) pp. 11–12.

Marshall et al. "Unidentified Curved Bacilli in the Stomach of Patients with Gastritis and Peptic Ulceration" *The Lancet* (Jun. 15, 1984) vol. 1, pp. 1311–1315.

Martin et al. "Difference in relapse rates of duodenal ulcer after healing with cimetidine or tripotassium dicitrato bismuthate" *The Lancet* (Jan. 3, 1981), pp. 7–10.

Matuszewska et al. "Acidic Fibroblast Growth Factor: Evaluation of Topical Formulations in a Diabetic Mouse Wound Healing Model" *Pharmaceutical Research* (1994), vol. 11, No. 1, pp. 65–71.

McDowell, et al. "Diagnosing and Treating Halitosis" *JADA*, vol. 124 (Jul. 1993) pp. 55–64.

McLean et al. "Microbes, Peptic Ulcer and Relapse Rates with Different Drugs" *The Lancet* (Sep. 1, 1984) vol. 2, pp. 525–526.

McNulty et al. "Campylobacter pyloridis and associated gastritis: Investigator blind, placebo controlled trial of bismuth salicylate and erthyromycin ethylsuccinate" *British Medical Journal,* (Sep. 13, 1986) vol. 293, pp. 645–649.

McNulty et al. "Spiral Bacteria of the Gastric Antrum" *The Lancet* (May 12, 1984) vol. 1, p. 1068.

McNulty et al. "Successful therapy of Campylobacter pyloridis gastrinitis" *Abstracts of Papers* (May 1986), p. 1547 [abstract only].

McNulty et al. "Susceptibility of Clinical Isolates of Campylobacter pyloridis to 11 Antimicrobial Agents" *Antimicrobial Agents and Chemotherapy* (Dec. 1985) vol. 28, No. 6, pp. 837–838.

Morris et al. "Ingestion of Campylobacter pyloridis causes gastritis and raised fasting gastric pH" *The American Journal of Gastroenterology* (1987), vol. 82, No. 3, pp. 192–199.

Mustofa et al. "Pharmacokinetics of metronidazole in saliva" *International Journal of Clinical Pharmacology, Therapy and Toxicology* (Dec. 1991) vol. 29, No. 12, pp. 474–478.

Nakao et al. "Antibacterial Properties of Lansoprazole Alone and in Combination with Antimicrobial Agents against *Helicobacter pylori*" *Eur. J. Clin. Microbiol. Infect. Dis.*, vol. 14, No. 5 (1995) pp. 391–399.

Nakao. "Antibacterial Properties of Lansoprozole Alone and in Combination with Antimicrobial Agents Against *Helicobacter pylori*" *J. Clin. Gastroenterol.*, vol. 20, supp. 1 (1995) pp. S32–S37.

Navarranne "Treatment of spasmodic and psychosomatic colopathies by a cicatrisant, antiseptic and anxiolytic medication combination" *Therapie* (1967) vol. XXII, pp. 419–426.

Nguyen et al. "Detection of *Helicobacter pylori* in Dental Plaque by Reverse Transcription–Polymerase Chain Reaction" *Journal of Clinical Microbiology* (Apr. 1993) vol. .31, No. 4, pp. 783–787.

Norfleet "Helicobacter halitosis" *J. Clin. Gastroenterol.* (1993) vol. 16, No. 3 [letter only].

O'Connor et al. "Vitamin C in the human stomach; relation to gastric PH, gastroduodenal disease and possible sources" *Gut* (1989) vol. 30, pp. 436–442.

Olsson et al. "*H. pylori* in dental plaques" *The Lancet* (Apr. 10, 1993) vol. 341, pp. 956–957.

Parsonett "*Helicobacter pylori* infection. *Helicobacter pylori* and gastric cancer" *Gastroenterology Clinics of North America* (Mar. 1993) vol. 22, No. 1 pp. 89–104.

Rauws, "Cure of duodenal ulcer associated with eradication of *Helicobacter pylori*" *The Lancet,* vol. 335, pp. 1233–1235.

Rauws, et al. "Campylobacter pyloridis–Associated Chronic Active Antral Gastritis. A prospective study of its prevalence and the effects of antibacterial and antiulcer treatment" *Gastroenterology.* vol. 94 (1988) pp. 33–40.

Recavarren–Arce et al. "*Helicobacter pylori* and progressive gastric pathology that predisposes to gastric cancer" *Scand. J. of Gastroenterol* (1991) vol. 26, supp. 181, pp. 52–57.

Reed et al. "Effect of ascorbic acid on the intragastric environment in patients at increased risk of developing gastric cancer" *larc Scientific Publications* (1991) vol. 105, pp. 139–142.

Reynolds (editor) Martindale *The Extra Pharmacopoeia* 28$^{th}$ Ed (1982) pp. 927–930.

Rosenberg et al. "Day–Long Reduction of Oral Malodor by a Two–Phase Oil: Water Mouthrinse as compared to chlorhexidine and placebo rinses" *J. Periodontol* (1982) vol. 63, No. 1, pp. 39–43.

Sakaki et al. "An endoscopic study on relationship between *Helicobacter pylori* infection and endoscopic gastric ulcer scars" *Digestive Diseases and Sciences* (May 1995) vol. 40, No. 5, pp. 1087–1092.

Schmitt. "New Methods of Delivery of Amphotericin B" *Clinical Infectious Diseases,* vol. 17, supp. 2 (1993), pp. S501–S506.

Schorah et al. "Gastric juice ascorbic acid: effects of disease and implications for gastric carcinogenesis" *Clin Nutr* (1991) vol. 53, pp. 287S–293S.

Seppälä, "*H pylori* and gastric ulcer disease" *Helicobacter pylori Basic Mechanisms to Clinical Cure* (1994) pp. 429–436.

Shreeve et al. "Comparison of cimetidine and tripotassium dicitrato bismuthate in healing and relapse of duodenal ulcers" *Digestion* (1983) vol. 28, No. 2 pp. 96–101.

Sipponen et al. "Long–term consequences of *H. pylori* infection: time trends in *H. pylori* gastritis, gastric cancer and peptic ulcer disease" *Helicobacter pylori Basic Mechanisms to Clinical Cure* (1994) pp. 372–380.

Skirrow "Report on the Session: Infections due to campylobacters other that *C. jejuni* and *C. Coli.*" *Campylobacter II*, Proceedings of the Second International Workshop on Campylobacter Infections (1983) pp. 5–10.

Sobala et al. "Acute *Helicobacter pylori* infection: clinical features, local and systemic immune response, gastric mucosal histology, and gastric juice ascorbic acid concentrations" *Gut* (1991) vol. 32, pp. 1415–1418.

Sobala et al. "Ascorbic Acid In The Human Stomach" *Gastroenterology* (1989) vol. 97, pp. 357–363.

Steer "Surface morphology of the gastroduodenal mucosa in duodenal ulceration" *Gut* (1984) vol. 25, pp. 1203–1210.

Steffen et al. "abstract No. 1623" *Biological Abstracts* (1986) vol. 82, No. 1626 [abstract only].

Steinhoff et al. "Bismuth Subsalicylate Therapy of Viral Gastroenteritis" *Gastroenterology* (1980) (Jun. 1980) vol. 78, No. 6 pp. 1495–1499.

Stolte "*Helicobacter pylori:* Auch ein Krebserreger?" *GASTRO–LIGA Report* (Mar./Apr. 1994) pp. 5–7 [in German].

Stolte "*Helicobacter pylori*–syndrom: von der gastritis bis hin zum malignom" (May 1992) pp. 3–10 [in German].

Sutton. "Gastric ulcer healing with tripotassium dicitrato bismuthate and subsequent relapse" *Gut* vol. 23 (1982), pp. 621–624.

Tiomny et al. "Halitosis and *helicobacter pylori*" *J. Clin Gastroenterol.,* (1992) vol. 15, No. 3, pp. 236–237.

Tytgat et al. "DE–NOL® in the treatment of peptic ulcer. Proceedings of the DE–NOL® symposium" *Scand J of Gastroenterology* (Jun. 15, 1982), pp. iv–61.

Wagner et al. "Bismuth subsalicylate in the treatment of $H_2$ blocker resistant duodenal ulcers: role of *Helicobacter pylori*" *Gut* (1992) vol. 33, pp. 179–183.

Wallace. ed. "Can Germs Cause Gastritis and Ulcers?" *Harvard Medical School Health Letter,* (Nov. 3, 1987), pp. 2–4.

Warren, J. with reply from B. Marshall "Unidentified Curved Bacilli on Gastric Epithelium in Active Chronic Gastritis" *The Lancet* (Jun. 4, 1983) vol. 1 p. 1273–1275.

Wieriks et al. Pharmacological Properties of Colloidal Bismuth Subcitrate (CBS, DE–NOL®) *Scand. J. Gastroenterol.,* (1982), vol. 17, supp. 80, pp. 11–16.

Wormsley "Relapse of duodenal ulcer" *British Medical Journal* (Dec. 6, 1986) vol. 293, p. 1501 [letter only].

Wu et al. "Platelet–derived Growth Factor–BB Accelerates Wound Closure in a New Mesenter Culture Model Without Macrophages" *Annals of Plastic Surgery* (Aug. 1994), vol. 33, No. 2, pp. 155–161.

Drumm et al. "Association of *Campylobacter Pylori* on the Gastric Mucosa With Antral Gastritis in Children" *The New England Journal of Medicine* (Jun. 18, 1987), vol. 316, No. 25, pp. 1557–1599.

Tytgat et al. "*Campylobacter pylori* Diagnosis and Treatment" *Journal Clinical Gastroenterol,* vol. II, Suppl. 1, 1989, pp. S49–S53.

Tytgat et al. "*Helicobacter pylori:* Casual agent in peptic ulcer disease?" *Working Party Reports,* (1990) pp. 36–45.

Piper, "Bactria, gastritis, acid hyposecretion and peptic ulcer" *The Medical Journal of Australia,* vol. 142, Apr. 15, 1985, p. 431.

McLean et al. "Microbes, Peptic Ulcer, and Relapse Rates With Different Drugs", *The Lancet,* Sep. 1, 1984, pp. 525–526.

Lambert et al. "Effect of Colloidal Bismuth (De–Nol) on Healing and Relapse of Duodenal Ulcers—Role of Campylobacter Pyloridis", Abstract No. 91, IVth International Workshop of Campylobacter Infections, Goteberg, Sweden, Jun., 1987, p. 383.

Goodwin et al. "Clearance of *Campylobacter pylori* and reduced duodenal ulcer relapse with bismuth and tinidazole compared to cimetidine", Abstract No. 60, IVth International Workshop on Campylobacter Infections, Goteberg, Sweden, Jun. 1987, pp. 368–369.

Malfertheiner et al. "Chronic Erosive Gastritis—a Therapeutic Approach with Bismuth", *Scandinavian Journal of Gastroenterology,* vol. 23, Supp. 142, 1988, pp. 87–92.

"Wismut", XV 3, pp. 789–791.

Goodwin et al. "Transfer of *Campylobacter pylori* and *Campylobacter Mustelae* to Helicobacter gen. nov. as *Helicobacter pylori* comb. nov. and *Helicobacter Mustelae* comb. nov., Respectively", *International Journal of Systematic Bacteriology,* Oct. 1989, vol. 39, No. 4 pp. 397–405.

Medline Abstract of: Lambert, J.R.; Dunn, K.; Borromeo, M.; Korman, M. G. "*Campylobacter pylori*—a role in non–ulcer dyspepsia?"; *Scandinavian Journal of Gastroenterology. Supplement* (1989), 160, 7–13, one page.

CA Abstract AN 1993:421501 of: Nguyen, A. M. H.; Engstrand, L.; Genta, R. M.; Graham, D. Y.; El–Zaatari, F. A. K. "Detection of *Helicobacter pylori* in dental plaque by reverse transcription–polymerase chain reaction"; *J. Clin. Microbiol.* (1993), 31(4), 783–7, one page.

Derwent Abstract No. XP–002176392 of Japanese Patent Application 08 020543, Jan. 23, 1996 (Inventor Narayan K. Athanikar).

* cited by examiner

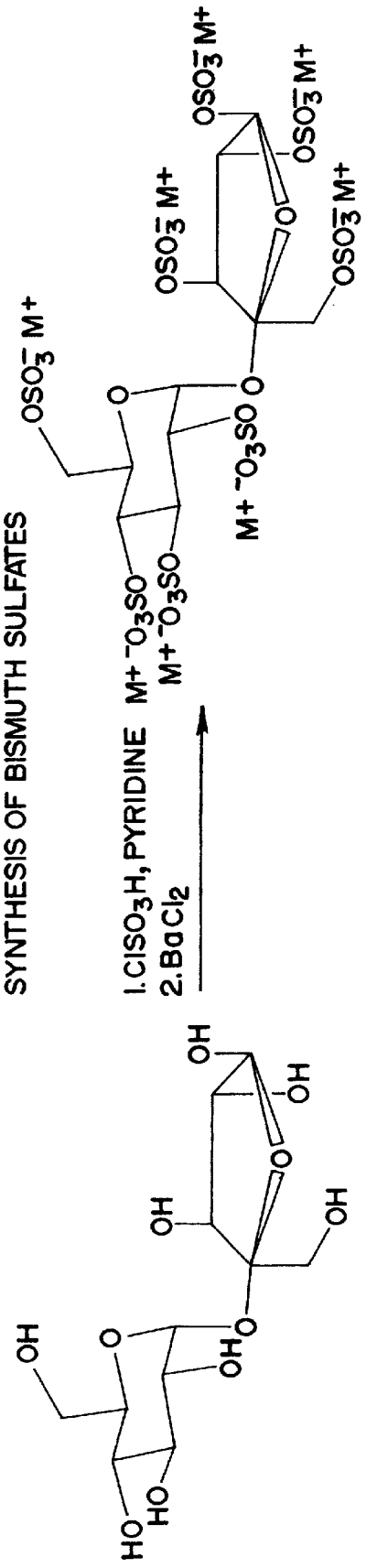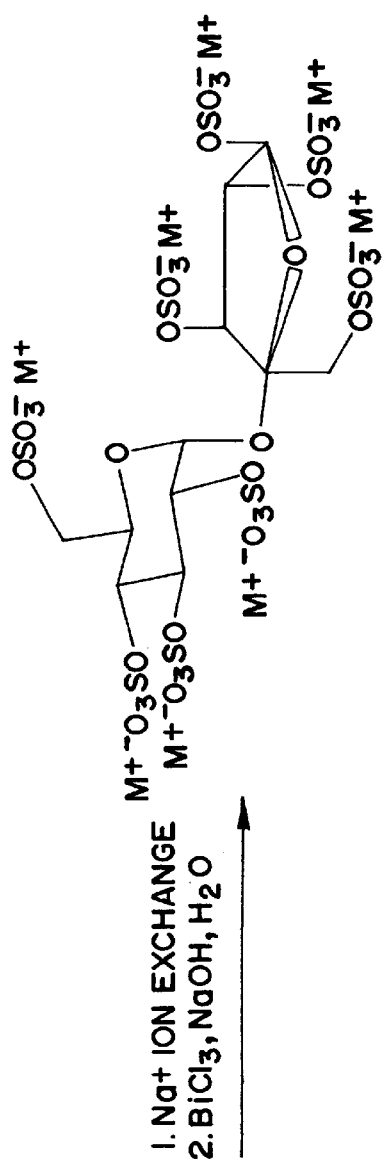
FIG. 1 SYNTHESIS OF BISMUTH SULFATES
THE ASCORBIC ACID-DERIVED MOLECULES WILL BE SYNTHESIZED IN A COMPLETELY ANALOGOUS SET OF REACTIONS

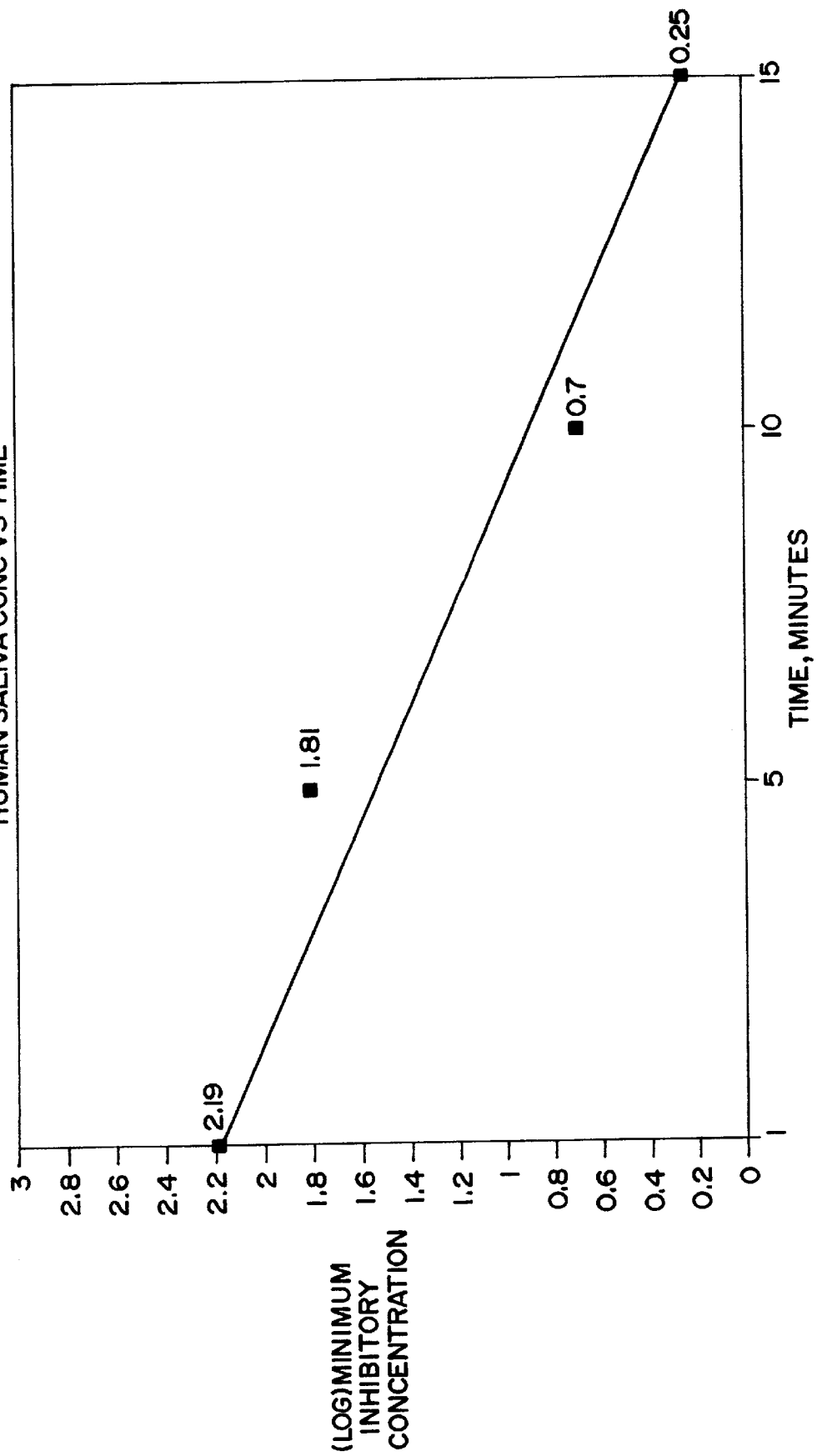

BISMUTH-CONTAINING COMPOUNDS IN TOPICAL DOSAGE FORMS FOR TREATMENT OF CORNEAL AND DERMAL WOUNDS

This application is a continuation of application Ser. No. 09/253,559, filed Feb. 19, 1999, abandoned, which is a continuation of U.S. application Ser. No. 08/918,322 filed Aug. 26, 1997 and now abandoned which is a continuation-in-part of co-pending U.S. application Ser. No. 08/518,971, filed Aug. 24, 1995, now abandoned, which in turn is a continuation-in-part of U.S. application Ser. No. 08/385,060, filed Feb. 7, 1995, now abandoned, which in turn claims priority under 35 U.S.C. §119 to Japanese Application No. 6-93518, filed May 2, 1994. All of the above-identified applications are expressly incorporated herein by reference.

BACKGROUND OF THE INVENTION

Until recently, excessive gastric acidity and mental stress were thought to be major pathophysiological reasons for occurrence of peptic ulcers. In the early 1980, Marshall and Warren (Warren, Lancet, 1:1273–1275, 1983 and Marshall et al., Lancet, 2:1311–1315, 1984) first reported an unidentified curved bacilli in the stomach of patients with gastritis and peptic ulcers. These bacilli, which later were identified as a gram negative spiral bacterium and named *Helicobacter pylori* (Goodwin et al., Int. J. Syst. Bacteriol. 32:397–405, 1989), have been demonstrated to be associated with gastritis and peptic ulcers (Buck et al., J. Infect. Dis. 153:664–669, 1986 and Graham, Gastroenterology 26:615–625, 1989), and are thought to be transmitted by person-to-person contact. *H. Pylori* in the dental plaque (Nguyen et al., Journal of Clinical Microbiology 31(4):783–787, 1993; Desai et al., Scandinavian Journal of Gastroenterology 26:1205–1208, 1991; and Lambert et al., Lancet 341(8850):957, 1993), and have also shown that standard oral hygiene practice does not help reduce *H. Pylori* presence in the oral cavity (Nguyen et al., Journal of Clinical Microbiology 31(4):783–787, 1993). As a result of these recent discoveries associating bacterial infection in the causation of peptic ulcer disease, questions regarding the previously established paradigms of ulcer treatment and healing processes have been raised.

$H_2$ receptor blockers which suppress acid secretion, such as cimetidine (Tagamet®) and ranitidine (Zantac®), have been used to treat and heal duodenal ulcers (Jones et al., Gut. 2:1120–1127, 1987; McIsaac et al., Aliment. Pharmacol. Therap. 1:369–381, 1987; and Boyed et al., Amsterdam:Excerpta Medica, 14–42, 1984). Recently, however, a number of clinical investigations have demonstrated that 70-80% of healed duodenal ulcers reoccur within the next year (Goodwin et al., Int. J. Syst. Bacteriol 22:397407, 1989), and that these drugs do not reverse the tendency for ulcers to form (Wormsley, British Medical Journal 293:1501, 1986; Gudman et al., British Medical Journal i:1095–1097, 1978; and Bardhan et al., British Medical Journal 29:621–623, 1982).

For many years, bismuth compounds have been used for treating ulcers. Clinical investigations comparing the efficacy of CBS (also known as tripotassium dicitrato bismuthate (TDB)) with placebo (Lambert, Scandinavian Journal of Gastroenterology 26(Supplement 185):13–21, 1991), cimetidine (Bianchi, et al., Lancet 2:698, 1984), and ranitidine (Bianchi et al., Gut. 2:565, 1984; Lee et al., Lancet 1:1299–1301, 1985; and Dobrilla et al., Gut. 22:181–187, 1988) in initial healing and relapse rates of duodenal ulcers, have shown significantly lower relapse rates in patients treated with CBS. The therapeutic efficacy of CBS (and other bismuth compounds), in healing duodenal ulcers and lowering relapse rates, is attributed to its specific antibacterial activity against *H. Pylori* (McNutty et al., Antimicrobial Agents Chemotherapy 2:837–838, 1985; Lambert et al., Antimicrob. Agents Chemotherapy 2:510–511, 1986; and Good win et al., J. of Antimicrobial Agents Chemotherapy 17:309–314, 1986). The minimum inhibitory concentration (MIC) for CBS against *H. Pylori* is reported to be 8 mg/L (Lambert et al., Antimicrob. Agents Chemotherapy 3:510–511) and the range is 4–32 mg/L (Lambert et al., Antimicrob. Agents Chemotherapy 3:510–511).

In addition to its bacteriocidal activity, CBS has been demonstrated to enhance mucus glycoprotein secretion, strengthen viscoelastic gel properties of mucus, cause increased concentration of epithelial growth factor (EGF) in ulcer tissue, and stimulate prostaglandin synthesis in the gastric antral mucosa (Lee, Scandinavian Journal of Gastroenterology 26(Supplement 185):1–6, 1991). These gastroprotective properties of CBS may contribute to the initial healing of duodenal ulcers and the observed lower rates of relapse by returning the gastric mucosal cells to normal physiologic function. The gastroprotective effects of CBS in prevention of gastric lesions induced by various ulcerogenic agents and the mechanism of ulcer healing have been demonstrated in animal studies (Konturek et al., Digestion 37(Supplement 2):8–15, 1987 and Konturek et al., Scandinavian Journal of Gastroenterology 21(Supplement 122):6–10, 1986).

Because of the finding that bismuth is an effective antibacterial agent against *H. Pylori*, concomitant dosages of bismuth-containing compounds with other anti-ulcer drugs have been increasingly applied in many clinical cases for treatment of peptic ulcers. The most commonly used regiments include double or triple therapy with bismuth; meanwhile, some recent reports regarding quadruple therapy (wherein a proton pump inhibitor is added to triple therapy) have shown eradication rates of over 90%, but also cause severe side effects such as vomiting and diarrhea.

Additionally, while antibacterial therapy (bismuth and amoxycillin or doxycycline) was shown to be effective in eliminating *H. Pylori* from the gastric mucosa of duodenal ulcer patients, this therapy had no effect on the *H. Pylori* colonies in their dental plaque (Desai et al., Scandinavian Journal of Gastroenterology 26: 1205–1208, 1991, Nguyen et al., Journal of Clinical Microbiology 31(4):783–787, 1993). The continued presence of *H. Pylori* in the dental plaque raises the question of whether the relapse of duodenal ulcers is inevitable (Desai et al., Scandinavian Journal of Gastroenterology 26 :1205–1208, 1991 and Abraham et al., Indian Journal of Gastroenterology 9(4):265–6, Editorial, 1990).

Triple therapy, consisting of an antibiotic (amoxicillin, tetracycline or erythromycin), metronidazole, and bismuth compounds, has been reported to result in more than a 95% eradication rate for *H. Pylori*, and reduced ulcer relapse rate to less than 10% during a 12-month follow-up period (Graham et al., Gastroenterology 102:493–496, 1992 and Borody et al., Gastroenterology 102:A 44, 1992). It is interesting to note that metronidazole as a single agent has only 5% eradication rate for *H. Pylori*, but as a component of triple therapy, it increases the eradication rate to as high as 95%. When metronidazole-resistant strains of *H. Pylori* are encountered (about 25% of the *H. Pylori* strains are resistant), the eradication rate falls to about 50% (Logan et al., Lancet 3:1249–1252, 1991).

One possible explanation for this observed clinical efficacy of metronidazole in combination therapy is that metronidazole is actively secreted in the saliva (Mustofa et al., International Journal of Clinical Pharmacology, Therapy, and Toxicology 29(12):474–478, 1991) where it might be exerting its antimicrobial action against dental plaque-bound H. Pylori colonies. The typical steady state saliva represent 10 to 20 times the MIC for H. Pylori. Another antibiotic, Clarithromycin, a new-generation macrolide, which has shown a 40 to 60% cure rate as a single agent, is also secreted in the saliva. Therefore, it is reasonable to believe that in order to achieve nearly complete eradication of H. Pylori, and prevent peptic ulcer relapse, eradication of this organism from the oral cavity is essential. Colloidal bismuth subcitrate (CBS), the most effective single agent against H. Pylori, is however not absorbed significantly from the GI, and therefore, produces no salivary concentrations. But as a single agent, it is about 6 to 8 times more effective in eradicating H. Pylori than metronidazole. The present invention therefore is related to development of a therapeutic modality to effectively eradicate H. Pylori reservoir from the oral site, as well as the gastric mucosal wall.

Furthermore, recent clinical studies have implicated this insidious organism in gastric cancer (Parsonnet, Gastroenterology Clinics of America, *Helicobacter pylori* Infection, Dooley CP, Cohen, H. Guest Editors, Volume 22, No. 1, pp. 89–104, March 1993). A progression of gastric pathology from gastritis and ulcers to cancer involving H. Pylori has been described (Recavarren-Arie et al., Scandinavian Journal of Gastroenterology 26(Supplement 181):51–57, 1991). In addition to H. Pylori infection, low concentration levels of ascorbic acid in the gastric mucosa has been shown to be a risk factor for gastric cancer (Schorah et al., American Journal of Clinical Nutrition 53(Supplement 1):287S-293S, 1991 and Reed et al., Iarc Scientific Publications, 105:139–142, 1991). In patients suffering from dyspepsia, chronic gastritis, hypochlorhydria, and duodenal cancer, the intragastric concentrations of vitamin C were significantly lower (Sobala et al., Gastroenterology 97(2):357–363, 1989 and O'Conner et al., Gut 30(4):436–442, 1989). The present invention therefore also relates to therapies involving both bismuth compounds and ascorbic acid.

SUMMARY OF THE INVENTION

The invention relates to concomitant treatment with bismuth compounds and/or with other antibacterial compounds and/or with antibiotics in topical oral and peroral dosage forms to eradicate H. Pylori from its niches both in the dental plaque and in the gastric mucosa in order to improve the ulcer cure rate and prevent ulcer relapse. The invention also provides oral topical dosage forms with pharmaceutically usable bismuth compounds and/or antibacterial compounds and/or antibiotics that eradicate or reduce H. Pylori in dental plaque. The invention further provides for treatment with bismuth compounds and/or antibacterial compounds and/or antibiotics which are effective against *Campylobacter rectus* and *Treponema denticola* which are responsible for causing halitosis. The invention also provides bismuth compounds which have applications in wound healing, particularly in ocular and dermal wound healing.

BRIEF DESCRIPTION OF THE DRAWINGS

FIG. 1 is a generalized reaction diagram for the synthesis of bismuth sulfates.

FIG. 2 is a graph of human saliva concentration versus time which shows the release of bismuth from CBS chewing gum.

DETAILED DESCRIPTION OF THE INVENTION

Therefore, bismuth compound used in this invention should be a pharmaceutically acceptable antimicrobacterial agent against H. Pylori, such as colloidal bismuth subcitrate (CBS), bismuth subcitrate, bismuth citrate, bismuth salicylate, bismuth subsalicylate, bismuth subnitrate, bismuth subcarbonate, bismuth tartrate, bismuth subgallate, tripotassium dicitrato bismuthate and bismuth aluminate. Preferably, colloidal bismuth subcitrate (CBS), tripotassium dicitrato bismuthate, bismuth subcitrate, bismuth subsalicylate and their combination are chosen. More preferably, CBS and tripotassium dicitrato bismuthate are chosen. And further selection is made for CBS.

The structural formula of CBS is:

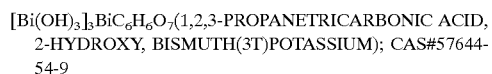

[Bi(OH)₃]₃BiC₆H₆O₇(1,2,3-PROPANETRICARBONIC ACID, 2-HYDROXY, BISMUTH(3T)POTASSIUM); CAS#57644-54-9

Other novel bismuth-containing compounds which are useful in the present invention are those described in Bos et al., U.S. Pat. No. 4,801,608 and in Serfortein, U.S. Pat. No. 4,153,685, both of which are expressly incorporated herein by reference. Other bismuth compounds, namely complexes of polysulfates, of polyhydroxy compounds such as sugars, sugar alcohols, and ascorbic acid and its derivatives, as well as alpha-D-glucopyranoside bismuth complex, beta-D-fructofuranosyl-oktakis (hydrogen sulfate) bismuth complex, and L-dihydro ascorbyl-tetrakis (hydrogen sulfate) bismuth complex are part of the present invention. A generalized reaction diagram for the synthesis of bismuth sulfates is shown in FIG. 1. These novel compounds will deliver bismuth more effectively and will have less side effects in treating H. Pylori positive gastro duodenal diseases. The compounds will lend themselves to controlled release oral dosage forms and oral topical dosage forms for eradication of H. Pylori in dental plaque.

Chemical structures of the compounds conceived in this invention are complexes of poly-sulfates and of poly-hydroxy compounds such as sugars, sugar alcohols, and ascorbic acid and its derivatives. These novel compounds will deliver bismuth more effectively and will have less side effects in treating H. Pylori positive duodenal ulcers and gastritis. These compounds moreover lend themselves to controlled release oral dosage forms and oral topical dosage forms for eradication of H. Pylori in dental plaque.

Chemical structures of the compounds conceived in this invention are illustrated below:

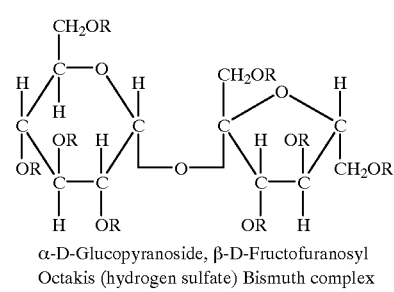

α-D-Glucopyranoside, β-D-Fructofuranosyl
Octakis (hydrogen sulfate) Bismuth complex

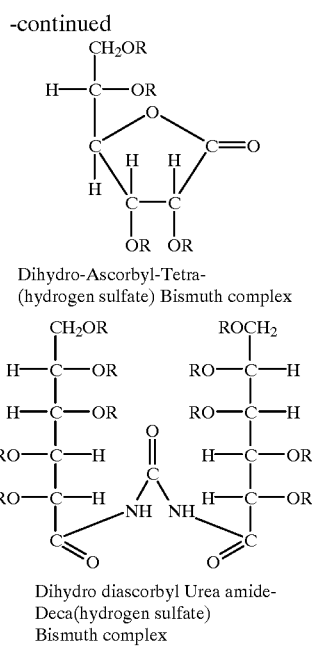

Dihydro-Ascorbyl-Tetra-(hydrogen sulfate) Bismuth complex

Dihydro diascorbyl Urea amide-Deca(hydrogen sulfate) Bismuth complex

The ascorbic acid-derived molecules are synthesized in a manner completely analogous to the reaction diagram for synthesis of bismuth sulfates set forth above. These compounds can also be used in embodiments relating to would healing as described below.

In addition to antibacterial bismuth-compounds and antibiotics to the oral cavity for reduction/elimination of *Helicobacter pylori* in the oral cavity as a means of treatment and prevention of gastrointestinal diseases including peptic ulcers, recurring gastritis, non-ulcer dyspepsia and gastric cancer. Antibiotics useful herein include, but are not limited to, Tetracycline, Amoxicillin, Ampicillin, Doxycycline, Erythromycin, Clarithromycin, Metronidazole, Tinidazole, Ciproflaxacin, Oflaxacin, Norflaxacin, Furazolidine, Nitrofurantoin. Antibacterials useful herein include, but are not limited to naturally occurring peptides and synthetic peptide antibacterials such as Lanthocins, and particularly, Nicin and related peptides, Proton pump inhibitors such as Omeprazole and Lansoprazole, Sanguinaria and other antibacterials obtained from plant sources, as well as bismuth-containing compounds.

The present methods utilize topical oral dosage forms to deliver bismuth compounds, antibiotics, and/or antibacterials directly to the oral cavity in concentrations sufficient to reduce or eliminate *H. Pylori* in tn oral cavity.

Each oral-topical dosage form of this invention is the one which can make it possible to release bismuth compound and/or antibacterial compounds and/or antibiotics into oral cavity in a predictable manner and result in appropriate antibacterial concentration. Those examples of such forms include a chewing-gum form, a chewable form including chewable tablets, lozenges, dental paints, viscous gels, dental implants, polymer film adhesives, a troche form, a toothpaste form, a gargling-gel form and mouth-rinse form. Preferably, a chewing-gum form and a troche form are chosen. Further, a chewing-gum form is most preferred due to its easy-to-use characteristic, predictable drug release and increased drug contact with dental surface. The chewing gum delivery system specially enables sustained contact of the antibacterial agents with the entire oral cavity and therefore, enhance bactericidal/bacteriostatic efficacy. We have already demonstrated that chewing gum formulation containing an antibacterial agent, colloidal bismuth subcitrate, releases the drug in a precise and reproducible fashion during a 15 minute chewing time. Chewable tablets, viscous gel formulations, and dental paint formulations also will be able to provide sustained concentration of antibacterial agents in the oral cavity.

Oral-topical dosage forms containing bismuth in this invention must release enough bismuth, antibiotic, and/or antibacterial into saliva for eradication of *H. Pylori* in the oral cavity. The minimum inhibitory concentration (MIC) of bismuth for *H. Pylori* varies in each bismuth compound. For instance, it is reported that the MIC of CBS for *H. Pylori* is 8 mg/L and its range is 4 to 32 mg/L.

Therefore, the dosage form should release bismuth into saliva up to at least two times the MIC, preferably a minimum of 2 to 10 times, most preferably 2 to 250 times. In order to achieve this level of release rate, the bismuth content per dosage form should be about 50 mg to 200 mg, preferably a minimum of 10 mg to 50 mg, most preferably 25 mg to 50 mg. For instance, each piece of CBS-containing chewing gum should contain approximately 50 mg to 200 mg of CBS, preferably a minimum of 10 mg to 50 mg, most preferably 25 mg to 50 mg.

Time release of each dosage form in this invention must be long enough to eradicate *H. Pylori*. Although the duration of time release varies in each bismuth compound and in each dosage form, it is desirable that at least 25% of the dose is released within 2 minutes, more preferably at least 35%, more preferably at least 45%, more preferably at least 55%, more preferably at least 65%, most preferably at least 75%, more preferably within 2 to 15 minutes, most preferably within 10 to 15 minutes.

In other preferred embodiments of the invention presented herein, a chewing gum drug delivery system is utilized to provide sustained concentration of bismuth compounds, antibiotics, and/or antibacterial compounds which are proven antibacterial agents against *H. Pylori* and anti-plaque agents to help these compounds penetrate the dental plaques to reach the site of *H. Pylori* infection. The chewing gum delivery system enables sustained contact of the antibacterial agents with the entire oral cavity and therefore, enhances bacteriocidal efficacy.

Where antibiotic and/or antibacterial agents other than bismuth are to be used, oral-topical dosage form in this invention must release enough antibiotic/antibacterial into saliva for eradication of *H. Pylori* from the oral cavity. The minimum inhibitory concentration (MIC) varies for each antibiotic/antibacterial agent. However, for most of the antibiotics listed in this invention, the MIC values are between less than 1 to 10 mcg/mL, or 1 to 10 mg/L.

Therefore, the topical-oral dosage from should release the anti-bacterial agent into saliva up to at least 2 times the MIC, preferably a minimum of 2 to 10 times, most preferably 2 to 100 times. In order to achieve this level of release, the antibacterial content per unit of dosage form should be about 10 to 100 mg, preferably a minimum of 5 to 50 mg, most preferably 10 to 25 mg. For instance, each piece of chewing gum should contain approximately 10 to 100 mg. of the antibiotic or antibacterial agent. Preferably a minimum of 5 to 50 mg, most preferably 10 to 25 mg.

The topical-oral dosage forms of this invention must release the antibiotic/antibacterial over an extended time. The duration of release should be at least 5 minutes, preferably 10 minutes, most preferably 15 minutes. Further, at least 25% of the dose is released within 5 minutes, more preferably at least 35%, more preferably at least 45%, more preferably at least 55%, more preferably at least 65%, most preferably at least 75% of the antibiotics/antibacterial content should be released within 5 minutes, preferably within 2 to 15 minutes, most preferably within 10 to 15 minutes.

In other preferred embodiment of this invention, a chewing gum delivery system is utilized to provide sustained concentration of antibiotic/antibacterial agent several times above its MIC for *H. Pylori* over at least 10 times.

The anti-plaque agents further contribute to improved efficacy by breaking down the plaque and exposing the bacterial colonies to the antibacterial agents. The chewing gum formulation containing CBS, antibiotic, and/or antibacterial releases the drug in a precise and reproducible fashion during a 15-minute chewing time. Anti-plaque agents include, but are not limited to, glucanase anhydroglucosidase, glucose oxidase, silicon oil, sanguinarine, and the like. Chewing gum formulations may optionally include crystalline sorbitol, sorbitol solution, mannitol, Nova-base™, or any other gum base, dextrans, cellulose derivatives, buffer salts, sweeteners, flavors, and the like.

Optionally, metronidazole can be added to CBS chewing gum to broaden the antimicrobial activity against *H. Pylori*.

Bismuth compounds embodied in these inventions also have been found to stimulate cellular production of growth factors, and therefore have applications in wound healing, specifically in ocular and dermal wound healing. Therefore, the present invention also contemplates use of novel bismuth complexes with sulfated polyhydroxy hydrophilic film-forming polymers to accelerate wound healing in ulcerative diseases of the eye, skin, and other mucosal tissues. For these embodiments, the invention involves synthesis of unique complexes of bismuth with partially sulfated hydrophilic film-forming polymers such as hydroxyprobyl cellulose, hydroxyethyl cellulose, hydroxypropyl-methyl cellulose, carboxymethyl cellulose, and polyvinyl alcohol. These compounds are formulated in unique film-forming solutions, aerosols, and gels for treatment of corneal ulcers, skin ulcers, gastric ulcers, and other wounds of the skin and mucous membranes. The general structures of this class of complexes are represented below:

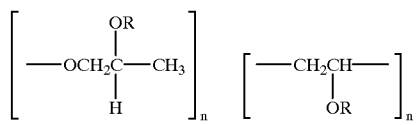

EXAMPLE 1

Preparation of Therapeutic Substance

To an aqueous solution of ammonia are added bismuth citrate, citric acid, and caustic potash in specific stoichiometric proportions, and at specific temperatures. The solution is examined for turbidity and, if required, additional volume of ammonia solution is added to render the solution clear. The solution is then filtered on a carbon bed and spray dried to obtain free-flowing powder material. The product is packaged in an air and moisture proof glass container.

EXAMPLE 2

Preparation of Topical Dosage Form

Brief general description of the preferred topical dosage form, chewing gum, is set forth as follows. Fully melt the gum base (at approximately 90° C.) in Brabender mixer, a jacketed mixer with sigma blades. Remove the hot water from the mixer jacket, allow to cool, and add lecithin and mix well. Cool further to approximately 50° C., and add liquid flavor and mannitol. Mix until uniform. Dry blend colloidal bismuth subcitrate in sorbitol, and blend sodium citrate in sorbo syrup. Add sorbitol and sorbo syrup blends to the gum base. Cool the product to 35° C., add flavor and sweetener and mix until smooth. Remove the product from the mixing kettle, roll to form a sheet of uniform thickness and score to produce chewing gum sticks weighing 2.5 g each. Wrap individual gum sticks in aluminum foil and place in plastic bags. Where the gum is to include antibiotic or antibacterial compounds, the agent is coated with a polymeric substance to mask any untoward taste or odor, and to further regulate its release in the saliva.

EXAMPLE 3

Composition of CBS-Containing Gum

Two variations of the 50 mg CBS gum (Table 1) were used. Both formulations used were identical with the exception that Formula-2 contained sodium citrate to impart a firmer texture, while Formula-1 did not.

TABLE 1

| FORMULATIONS OF THE GUM (APPROX. 2.5 gm A PIECE) | | | |
|---|---|---|---|
| Formula-1 | | Formula-2 | |
| CBS | 50.0 mg | CBS | 50.0 mg |
| Crystalline Sorbitol | 910.0 | Crystalline Sorbitol | 910.0 |
| Gum Base | 575.0 | Gum Base | 575.0 |
| Sorbitol Solution | 500.0 | Sorbitol Solution | 500.0 |
| Mannitol | 400.0 | Mannitol | 400.0 |
| Peppermint Oil | 25.0 | Peppermint Oil | 25.0 |
| Spray Dried Peppermint | 12.5 | Spray Dried Peppermint | 12.5 |
| Grade t Lecithin | 10.0 | Grade t Lecithin | 10.0 |
| Aspartame | 10.0 | Aspartame | 10.0 |
| Sodium Citrate | 10.0 | Total: | 2492.5 mg |
| | 2502.5 mg | | |

Colloidal Bismuth Subcitrate (CBS) and other bismuth compounds, including bismuth subcitrate, bismuth citrate, bismuth salicylate, bismuth subsalicylate, bismuth subnitrate, bismuth subcarbonate, bismuth tartrate, bismuth subgallate, tripotassium dicitrato bismuthate and bismuth aluminate. Preferably, colloidal bismuth subcitrate (CBS), tripotassium dicitrato bismuthate, bismuth subcitrate, bismuth subsaticylate are coated with the following coating agent to regulate their dissolution and salivary release: bee's wax, carnauba wax, shellac, cellulose acetate phthalate, methyl cellulose, propyl cellulose, hydroxy propylcellulose, ethyl cellulose, hydroxy propylmethylcellulose, ethylcellulose, polymethyl methacrylate, and Eudragit® polymers, polyvinyl pyrohidone, polyvinyl alcohol, etc.

Moderately water soluble bismuth compounds such as bismuth ascorbyl sulfate, bismuth sucrose sulfate, bismuth subascorbate, cyclodextrin bismuth sulfate are used in the chewing gum dosage form to produce sustained concentration in the saliva.

Synthetic and natural latex-based chewing gum bases are used to tightly enclose bismuth compounds and other antibacterial/antibiotic compounds to cause their gradual release in the saliva.

These formulation/composition modifications are designed to:

(1) provide control release of antibacterial/antibiotic compounds to increase their bactericidal efficacy against oral cavity/dental plaque bound *H. Pylori*; and (2) avoid/minimize oral cavity discoloration/blackening caused by quick or instant release of bismuth compounds in the saliva.

EXAMPLE 4

Measurement of Release Rate of Bismuth into Saliva

Among six healthy human subjects, who gave informed consent, three chewed the CBS-containing gum with sodium citrate, and the other three chewed CBS-containing gum without sodium citrate. The subjects chewed the gum samples for a total of 15 minutes. Saliva samples were collected at time interval of 0, 1, 5, 10, and 15 minutes of chewing. The saliva samples were then submitted to an analytical laboratory for bismuth analysis. Results are shown in Table 2.

TABLE 2

IN VIVO SALIVARY CONCENTRATION OF CBS FROM THE CHEWING GUM

| Formula | chewing time (min.) | saliva vol. (mL) | conc of Bi (ppm) | conc of active CBS (u/mL) | X MIC |
|---|---|---|---|---|---|
| formula-1 | 0 | 4.4 (± 0.5) | | | |
| | 1 | 3.3 (± 1.4) | 900.7 (± 239.1) | 1270.3 (± 334.7) | 148.7 (± 42.0) |
| | 5 | 5.4 (± 1.5) | 247.7 (± 112.3) | 363.3 (± 158.9) | 45.0 (± 19.9) |
| | 10 | 4.9 (± 1.3) | 28.0 (± 5.0) | 40.0 (± 6.6) | 5.0 (± 1.0) |
| | 15 | 5.2 (± 2.1) | 15.8 (± 17.8) | 25.7 (± 23.0) | 3.1 (± 2.7) |
| formula-2 | 0 | 7.2 (± 0.5) | | | |
| | 1 | 4.8 (± 1.9) | 888.3 (± 329.5) | 1257.0 (± 464.5) | 156.3 (± 58.0) |
| | 5 | 8.5 (± 1.7) | 326.0 (± 113.3) | 572.7 (± 159.7) | 63.7 (± 19.9) |
| | 10 | 7.5 (± 3.4) | 30.0 (± 9.5) | 42.3 (± 13.6) | 5.0 (± 1.7) |
| | 15 | 7.7 (± 3.8) | 10.7 (± 6.7) | 14.7 (± 9.2) | 1.8 (± 1.2) |

Saliva samples were analyzed for elemental bismuth in ppm units. The results were then converted to mg of active CBS per mL of saliva and also expressed as a multiple of minimum inhibitory concentration (MIC) of CBS for *H. Pylori*. As can be seen from the results (formula-2 of Table-3), the salivary concentrations of CBS are 156, 64, 5, and 1.8 times the MIC at 1, 5, 10 and 15 minutes, respectively. The constant bathing of the oral cavity from saliva containing sufficient concentration of CBS (2 to 5 times the MIC) for up to 15 minutes can be expected to further reduce the viable cells of *H. Pylori*. These results are plotted in FIG. 2 which a graph of human saliva concentration versus time.

EXAMPLE 5

Sensory Analysis of Chewing Gum

Sensory characteristics of the chewing gum were evaluated by the subjects during the 15 minutes of chewing. Again, three subjects chewed the CBS gum containing sodium citrate and three subjects chewed the CBS gum without sodium citrate. A nine point rating scale was used to evaluate each category (Tables 3 and 4).

TABLE 3

RESULTS OF SENSORY ANALYSIS RATING OF CBS GUM WITHOUT SODIUM CITRATE
(Formula-1)

| SENSORY CHARACTERISTICS | CHEWING TIME | | | |
|---|---|---|---|---|
| | 1 MIN | 5 MIN | 10 MIN | 15 MIN |
| Overall Flavor | 6.3 | 6.0 | 5.3 | 5.0 |
| (0 = dislike extremely, 8 = like extremely) | (±1.2) | (±1.0) | (±1.5) | (±1.0) |
| Flavor Intensity | 5.7 | 4.7 | 3.7 | 3.0 |
| (0 = none, 8 = very strong) | (±1.5) | (±1.2) | (±0.6) | (±1.0) |
| Chew Qualities | 6.0 | 6.0 | 5.3 | 5.0 |
| (0 = dislike extremely, 8 = like extremely) | (±1.0) | (±1.0) | (±1.5) | (±1.0) |
| Unpleasant Aftertaste | 0.0 | 0.0 | 0.0 | 0.0 |
| (0 = none, 8 = very strong) | (±0.0) | (±0.0) | (±0.0) | (±0.0) |

TABLE 3-continued

RESULTS OF SENSORY ANALYSIS RATING OF CBS GUM WITHOUT SODIUM CITRATE
(Formula-1)

| SENSORY CHARACTERISTICS | CHEWING TIME | | | |
|---|---|---|---|---|
| | 1 MIN | 5 MIN | 10 MIN | 15 MIN |
| Overall Qualities | 6.3 | 6.0 | 5.7 | 5.3 |
| (0 = dislike extremely, 8 = like extremely) | (±1.2) | (±1.0) | (±1.2) | (±1.5) |

TABLE 4

RESULTS OF SENSORY ANALYSIS RATING OF CBS GUM WITHOUT SODIUM CITRATE
(Formula-2)

| SENSORY CHARACTERISTICS | CHEWING TIME | | | |
|---|---|---|---|---|
| | 1 MIN | 5 MIN | 10 MIN | 15 MIN |
| Overall Flavor | 6.7 | 5.7 | 4.7 | 4.7 |
| (0 = dislike extremely, 8 = like extremely) | (±0.6) | (±1.5) | (±1.2) | (±1.2) |
| Flavor Intensity | 6.7 | 6.0 | 5.0 | 3.7 |
| (0 = none, 8 = very strong) | (±0.6) | (±0.0) | (±1.0) | (±1.5) |

TABLE 4-continued

RESULTS OF SENSORY ANALYSIS RATING OF CBS GUM
WITHOUT SODIUM CITRATE
(Formula-2)

| SENSORY CHARACTERISTICS | CHEWING TIME | | | |
|---|---|---|---|---|
| | 1 MIN | 5 MIN | 10 MIN | 15 MIN |
| Chew Qualities (0 = dislike extremely, 8 = like extremely) | 4.7 (±2.1) | 5.0 (±2.0) | 4.3 (±1.5) | 4.3 (±0.6) |
| Unpleasant Aftertaste (0 = none, 8 = very strong) | 0.7 (±1.2) | 1.7 (±2.1) | 1.7 (±2.1) | 2.0 (±2.0) |
| Overall Qualities (0 = dislike extremely, 8 = like extremely) | 6.3 (±0.6) | 5.7 (±1.2) | 4.7 (±1.2) | 4.0 (±1.0) |

In general, there were no dramatic differences in the sensory analysis between the two formulas. The sensory panel clearly shows that both chewing gum formulations have a desirable level of flavor and taste, and cause a ninimal unpleasant aftertaste after chewing.

EXAMPLE 6

Topical Safety

Topical safety was evaluated in the six volunteers for up to 60 minutes after administration of the gum. The subjects were asked to report any adverse effects such as discomfort or irritation in the oral cavity.

There were no reports of any discomfort or irritation in the oral cavity by any of the subjects at either the 15 or 60 minute post administration time periods.

EXAMPLE 7

Storage Stability Study

Samples of CBS-containing gum (50 mg) were wrapped individually in foil wrappers. The sticks of gum were then placed in foil laminate bags, sealed, and placed in storage. Storage conditions include 40° C. and room temperature (RT). The duration of the stability testing was 90 days. The results are shown in Tables 5–8 below.

TABLE 5

THREE MONTH STABILITY DATA
IN VIVO SALIVARY CONCENTRATIONS IN HUMAN SUBJECTS
OF CBS FROM THE 50 MG CBS CHEWING GUM
(Mfg. August 1993, Batch No. CBS-50CG-0002)

| TIME/CONDITION | CHEWING TIME (min) | SALIVA VOLUME (mL) | CONC OF Bi (ppm) | CONC OF Bi (pg/mL) | CONC OF ACTIVE CBS (pg/mL) | % MIC |
|---|---|---|---|---|---|---|
| ZERO TIME | 0 | 4.2 (± 1.6) | NA | NA | NA | NA |
| | 1 | 4.9 (± 4.5) | 1937.3 (± 753.5) | 1937.3 (± 753.5) | 2729.0 (± 1060.2) | 341.0 (± 132.7) |
| | 5 | 6.4 (± 3.1) | 437.0 (± 152.1) | 437.0 (± 152.1) | 615.7 (± 214.5) | 77.0 (± 26.9) |
| | 10 | 3.9 (± 0.1) | 36.0 (± 28.6) | 36.0 (± 28.6) | 50.7 (± 40.5) | 6.4 (± 5.0) |
| | 15 | 4.5 (± 1.3) | 5.0 (± 4.6) | 5.0 (± 4.6) | 7.0 (± 6.6) | 0.9 (± 0.8) |
| 3 MONTHS/ 40° C. | 0 | 5.6 (± 1.4) | NA | NA | NA | NA |
| | 1 | 2.9 (± 1.8) | 1922.3 (± 511.8) | 1922.3 (± 511.8) | 2710.0 (± 751.9) | 331.6 (± 90.3) |
| | 5 | 5.6 (± 1.7) | 399.3 (± 278.1) | 363.7 (± 113.3) | 563.0 (± 329.3) | 70.3 (± 49.1) |
| | 10 | 5.3 (± 1.4) | 25.7 (± 11.4) | 30.0 (± 9.5) | 362.0 (± 160.5) | 45.4 (± 20.1) |
| | 15 | 4.9 (± 0.4) | 7.9 (± 4.9) | 10.7 (± 6.7) | 10.8 (± 6.8) | 1.4 (± 0.9) |
| 3 MONTHS/ ROOM TEMP. | 0 | 5.1 (± 1.3) | NA | NA | NA | NA |
| | 1 | 4.1 (± 1.5) | 1240.0 (± 458.7) | 1240.0 (± 458.7) | 1748.0 (± 646.6) | 218.0 (± 180.6) |
| | 5 | 7.2 (± 2.3) | 518.7 (± 118.7) | 518.7 (± 118.7) | 731.3 (± 167.6) | 51.0 (± 21.0) |
| | 10 | 6.0 (± 2.2) | 12.5 (± 10.4) | 12.5 (± 10.4) | 17.7 (± 14.6) | 2.1 (± 1.8) |
| | 15 | 5.6 (± 1.6) | 4.5 (± 2.2) | 4.5 (± 2.2) | 6.0 (± 2.6) | 0.7 (± 0.3) | n = 3 for each group

TABLE 6

THREE MONTH STABILITY DATA
RESULTS OF SENSORY ANALYSIS RATING OF 50 MG CBS GUM
(Mfg. August 1993, Batch No. CBS-50CO-0002)

| | SENSORY CHARACTERISTIC | CHEWING TIME | | | |
|---|---|---|---|---|---|
| | | 1 MIN | 5 MIN | 10 MIN | 15 MIN |
| ZERO TIME | OVERALL FLAVOR | 6.7 (± 0.6) | 6.3 (± 0.6) | 5.3 (± 0.6) | 5.3 (± 0.6) |
| | FLAVOR INTENSITY | 6.3 (± 1.2) | 5.3 (± 1.2) | 4.0 (± 1.0) | 4.0 (± 1.0) |
| | CHEW QUALITIES | 6.7 (± 0.6) | 6.3 (± 0.6) | 5.7 (± 0.6) | 5.3 (± 0.5) |
| | UNPLEASANT AFTERTASTE | 0.0 (± 0.0) | 0.0 (± 0.0) | 0.0 (± 2.1) | 0.0 (± 0.0) |
| | OVERALL QUALITIES | 6.7 (± 0.6) | 6.3 (± 0.6) | 5.7 (± 0.6) | 5.3 (± 1.2) |
| 3 MONTHS/ 40° C. | OVERALL FLAVOR | 6.0 (± 0.6) | 4.7 (± 0.6) | 2.7 (± 1.2) | 2.7 (± 1.2) |
| | FLAVOR INTENSITY | 5.3 (± 1.2) | 3.0 (± 0.0) | 2.3 (± 0.6) | 2.0 (± 1.0) |
| | CHEW QUALITIES | 5.7 (± 0.6) | 5.0 (± 1.0) | 4.3 (± 0.6) | 4.3 (± 0.6) |

TABLE 6-continued

THREE MONTH STABILITY DATA
RESULTS OF SENSORY ANALYSIS RATING OF 50 MG CBS GUM
(Mfg. August 1993, Batch No. CBS-50CO-0002)

| | SENSORY CHARACTERISTIC | CHEWING TIME | | | |
|---|---|---|---|---|---|
| | | 1 MIN | 5 MIN | 10 MIN | 15 MIN |
| | UNPLEASANT AFTERTASTE | 0.3 (± 0.6) | 0.3 (± 0.6) | 0.0 (± 0.0) | 0.0 (± 0.0) |
| | OVERALL QUALITIES | 6.0 (± 0.0) | 4.3 (± 0.6) | 2.7 (± 0.6) | 2.3 (± 0.6) |
| 3 MONTHS/ | OVERALL FLAVOR | 6.3 (± 0.6) | 6.3 (± 0.6) | 5.3 (± 0.6) | 4.3 (± 0.6) |
| ROOM TEMP. | FLAVOR INTENSITY | 5.7 (± 1.5) | 5.3 (± 1.5) | 4.3 (± 1.5) | 4.0 (± 1.7) |
| | CHEW QUALITIES | 6.0 (± 1.0) | 6.0 (± 1.0) | 5.3 (± 0.6) | 4.3 (± 0.6) |
| | UNPLEASANT AFTERTASTE | 0.0 (± 0.0) | 0.0 (± 0.0) | 0.0 (± 0.0) | 0.0 (± 0.0) |
| | OVERALL QUALITIES | 6.3 (± 0.6) | 6.3 (± 0.6) | 5.3 (± 0.6) | 4.7 (± 1.2) |

Note: n = 3 for each analysis
Rating Scale:
0 = dislike extremely, 8 = like extremely for: Overall Flavor, Chew Quality, Overall Quality
0 = none, 8 = like extremely for: Flavor Intensity
0 = none, 8 = very strong for: Unpleasant Aftertaste

TABLE 7

EXPONENTIAL REGRESSION DATA OF TIME VS SALIVARY CONCENTRATION
EXPRESSED AS % MIC

| | Initial Test Lot | Stability Lot # CBS-50CG-0002 | | | Clinical Lot |
|---|---|---|---|---|---|
| | # CBS-50CG-0001 | Zero Time | 3 mo./RT | 3 mo./40° C. | # CBS-50CG-0003 |
| A (intercept) | 240.0 | 563.1 | 575.7 | 422.3 | 446.5 |
| b (slope) | −0.339 | −0.432 | −0.361 | −0.448 | −0.426 |
| r (correlation coefficient) | 0.992 | 0.998 | 0.948 | 0.971 | 0.959 |
| K (pseudo first order rate constant) | −0.339 | −0.432 | −0.361 | −0.448 | −0.426 |
| $t_{0.5}$ (min.) | 2.04 | 1.60 | 1.92 | 1.55 | 1.63 |

Mean $t_{0.5}$ = 1.748 (± 0.218)

TABLE 8

RELEASE OF CBS FROM THE CHEWING GUM AFTER
15 MINUTES OF CHEWING BY HUMAN SUBJECTS

| | Stability Lot # CBS-50CG-0002 | | | Clinical |
|---|---|---|---|---|
| | Zero Time | 3 mo./RT | 3 mo./40° C. | # CBS-50CG-0003 |
| Mg CBS/2.5 g gum Before chewing (%) | 45.6 (100) | 44.5 (100) | 46.1 (100) | 46.2 (100) |
| Mg CBS/2.5 g gum After 15 min chewing (%) | 3.5 (7.6) | 4.0 (9.0) | 4.5 (9.8) | 3.8 (100) |

Mean % of CBS Remaining in the gum after 15 min of chewing = 8.6 (± 1.0)

Each stick of the gums used for the stability study (1 for zero-time, 2 for three month, total 3 sticks) was from the same lot number. The results show that bismuth concentration remains stable over the tested time period.

EXAMPLE 8

Denture Material Exposure Study

An evaluation of CBS salivary concentration on various denture materials was conducted in order to test any potential staining effect of the CBS on denture materials. Artificial saliva was used (Table 9).

TABLE 9

THE COMPOSITION OF ARTIFICIAL SALIVA

| Ingredients | Concentration per Liter |
| --- | --- |
| Sodium Bicarbonate | 0.50 g |
| Sodium Phosphate, Dibasic, Dihydrate | 0.85 g |
| Calcium Chloride | 0.44 g |
| Magnesium Chloride | 0.06 g |
| Potassium Chloride | 1.40 g |
| Sodium Carboxyl Methyl Cellulose | 2.00 g |
| Phosphoric Acid to adjust pH to 6.4 Distilled Water | QS |

The test saliva was prepared by dissolving 0.500 g of colloidal bismuth subcitrate in 100 mL of the above artificial saliva. 500 mL of Artificial Saliva (RT) was placed in one of two identical glass jars with lids. In the other jar was placed 500 mL of the Artificial Saliva (RT) containing 0.50% of CBS. In each of the jars the denture material block and a magnetic stirrer was placed. The jars were then placed on the magnetic platform and set to agitate at a minimum rate. The denture materials that were exposed to artificial saliva containing CBS or placebo included (Table 10).

TABLE 10

DENTURE MATERIALS

1) Natural tooth with silver amalgam filling
2) Composite resin (used on anterior teeth for filling)
3) Denture base acrylic resin
4) Porcelain fused to metal
5) Partial denture metal frame
6) Acrylic tooth (artificial)
7) Natural tooth The four hour exposure of natural tooth and other denture materials to 0.5% CBS in artificial saliva with mild agitation did not cause any staining, discoloration, or changes in texture.

EXAMPLE 9

Clinical Efficacy Data

An open label, placebo-controlled pilot clinical study in ten patients with initial positive response for *H. Pylori* in the dental plaque has been initiated. Data from six patients (four patients treated with CBS 50 mg chewing gum six times-a-day and two patients treated with placebo chewing gum six times-a-day for fifteen days) has been obtained. The dental plaque samples from the patients were collected before treatment, day 7 and day 15 after treatment, and tested by microbiological culture and CLO test. The results are set forth in Table 11 below:

TABLE 11

| | | CLO | DUR POSITIVE (HRS:MINS) | CULTURE | SIDE EFFECTS (Stain/Odor) |
| --- | --- | --- | --- | --- | --- |
| TREATED GROUP (n = 4) | | | | | |
| Pt 1 | Day 0 | + | 1:00 | + | NE |
| 30/M | Day 7 | + | 1:45 | -ve | — |
| | Day 15 | + | 1:30 | -ve | — |
| Pt 2 | Day 0 | + | 2:15 | + | NE |
| 42/M | Day 7 | + | 1:30 | NA | — |
| | Day 15 | + | 4:00 | -ve | — |
| Pt 3 | Day 0 | + | 2:30 | + | NIL |
| 31/M | Day 7 | + | 4:30 | NA | NIL |
| | Day 15 | + | 5:30 | NA | NIL |
| Pt 4 | Day 0 | + | 2:30 | NA | NIL |
| 29/F | Day 7 | + | 4:00 | NA | NIL |
| | Day 15 | + | 5:30 | NA | NIL |
| Mean CLO response time after 15 days = 4.125 HR | | | | | |
| PLACEBO (n = 2) | | | | | |
| Pt 1 | Day 0 | + | 1:00 | NA | NIL |
| 26/M | Day 7 | + | 1:30 | NA | NIL |
| | Day 15 | + | 1:30 | NA | NIL |
| Pt 2 | Day 0 | + | 1:15 | NA | NIL |
| 28/M | Day 7 | + | 2:00 | NA | NIL |
| | Day 15 | 2:30 | NA | NIL | |
| Mean CLO response time after 15 days = 2.0 HR | | | | | |

NA = Not available
NE = Not evaluated (before chewing)

The data show that for patients treated with CBS 50 mg chewing gum and placebo chewing gum on day 15 the mean CLO response times are 4.125 hours and 2.0 hours, respectively. The longer CLO test response time for CBS 50 mg chewing gum group compared to the placebo chewing gum group is indicative of substantial reduction in *H. Pylori* density in the oral cavity of the active treatment group.

EXAMPLE 10

Toxicology

A number of animal toxicity studies and human clinical investigations have demonstrated safety of bismuth compounds, especially CBS, in therapeutic dose ranges. No toxicity has been reported in chronic daily administration of high doses of CBS (160, 320, and 640 mg/kg body weight representing 2, 4, and 8 times the human therapeutic dose respectively) in rats treated for three months or dogs treated for six months. See Wieriks et al., Journal of Gastroenterology 17(Supplement 80):11–16 (1982), incorporated herein by reference.

Long term safety of CBS and treatment of peptic ulcers at a standard dose of 480 mg (expressed as bismuthtrioxide) in four daily divided doses has been examined by Bader, Digestion 37(Supplement 2):53–59 (1987), incorporated herein by reference. CBS was first introduced in Europe in 1971 and since that time 1.5 million treatments have been dispensed. During eight years of use of CBS tablets [De-Nol(R)®] in Europe between 1978 and 1986 under a more comprehensive adverse reaction monitoring system, only 13 adverse reaction forms were completed. Five of these adverse reactions were ascribed to CBS: one case of headache, one case of stomach pain, one case of diarrhea, and two cases of allergy (mainly in the form of skin rashes). A high degree of safety of CBS in therapeutic applications for the treatment of peptic ulcers is reported in a recent review of pharmacology of bismuth-containing compounds by Lambert, Review of Infectious Diseases 13(Supplement 8):691–695 (1991), incorporated herein by reference. In reviewing safety and pharmacokinetics of CBS, Bennet, Scandinavian Journal of Gastroenterology 26(Supplement 185):29–35 (1991), incorporated herein by reference, has calculated the systemic bioavailability of bismuth after oral dosing of CBS to be in the range of 0.16 to 0.28% of the administered dose, and concluded that steady-state blood levels of 50–100 mg/mL are unlikely to cause any neurotoxicity.

EXAMPLE 11

Composition of Antibiotic or Antibacterial-Containing Gum

The chewing gum formulation comprises antibiotic or antibacterial agents in concentration ranges from 10 to 50 mg per piece of gum. The chewing gum-base consists of Crystalline Sorbitol, Gum Base, Sorbitol Solution, Mannitol, Peppermint Oil, Spray Dried Peppermint, Grade t Lecithin, Aspartame, and Sodium Citrate, as set forth in Table 1 above. The formulation may also contain Glucanase, Anhydroglucosidase, Glucose oxidase, Silicon oil, Sanguinarine and related compounds as anti-plaque agents. Caboxy methyl cellulose, Hydroxy propyl methyl cellulose, Polyethylene glycol, Poly methyl methacrylates, Acrylic acid copolymers and other polymers as coating agents.

Saliva samples are analyzed for antibiotic or antibacterial agents in ppm units. The results are then converted to mg of active agent per mL of saliva and also expressed as a multiple of minimum inhibitory concentration (MIC) of the agent for *H. Pylori*. The salivary concentrations of the agent are 156, 64, 5, and 1.8 times the MIC at 1, 5, 10 and 15 minutes, respectively. The constant bathing of the oral cavity from saliva containing sufficient concentration of the agent (2 to 5 times the MIC) for up to 15 minutes can be expected to further reduce the viable cells of *H. Pylori*; These results are plotted to show a graph of human saliva concentration versus time.

Sensory characteristics of the chewing gum are evaluated by the subjects during the 15 minutes of chewing. Again, three subjects chews the gum containing sodium citrate and three subjects chewed the gum without sodium citrate. A nine point rating scale is used to evaluate each category.

In general, there are no dramatic differences in the sensory analysis between the two formulas. The sensory panel shows that both chewing gum formulations have a desirable level of flavor and taste, and cause a minimal unpleasant aftertaste after chewing.

Topical safety is evaluated in the six volunteers for up to 60 minutes after administration of the gum. The subjects are asked to report any adverse effects such as discomfort or irritation in the oral cavity.

There are no reports of any discomfort or irritation in the oral cavity by any of the subjects at either the 15 or 60 minute post administration time periods.

Samples of the agent-containing gum (5mg) are wrapped individually in foil wrappers. The sticks of gum are then placed in foil laminate bags, sealed, and placed in storage. Storage conditions include 40° C. and room temperature (RT). The duration of the stability testing is 90 days.

Each stick of the gums used for the stability study (1 for zero-time, 2 for three month, total 3 sticks) is from the same lot number. The results show that bismuth concentration remains stable over the tested time period.

An evaluation of salivary concentration of the agent on various denture materials is conducted in order to test any potential staining effect of the CBS on denture materials. Artificial saliva is used (Table 9).

The test saliva is prepared by dissolving 0.500 g of the antibiotic or antibacterial agent in 100 mL of the above artificial saliva. 500 mL of Artificial Saliva (RT) is placed in one of two identical glass jars with lids. In the other jar is placed 500 mL of the Artificial Saliva (RT) containing 0.50% of the agent. In each of the jars the denture material block and a magnetic stirrer is placed. The jars are then placed on the magnetic platform and set to agitate at a minimum rate. The denture materials that are were exposed to artificial saliva containing the agent or placebo are included. The four hour exposure of natural tooth and other denture materials to 0.5% of the agent in artificial saliva with mild agitation does not cause any staining, discoloration, or changes in texture.

To assess clinical efficacy, patients with positive response for the presence of *H. Pylori* in the dental plaque/oral cavity are divided into two treatment groups. Group I is given placebo chewing gum to be chewed 2 or 6 times a day for 2 or 4 weeks. Group II is given chewing gum containing antibiotic/antibacterial agent to be chewed 2 or 6 times a day for 2 or 4 weeks. Patient's dental plaque/saliva samples are collected at time 0 (Pre-treatment) on days 7, 14, 28, and tested for *H. Pylori* presence and density. The incidence of *H. Pylori* presence in the placebo group and the active treatment group is compared. The group receiving the chewing gum containing antibiotic/antibacterial shows significantly lower incidence of *H. Pylori* presence in the dental plaque/saliva compared to placebo chewing gum group after 2 and 4 weeks of treatment.

EXAMPLE 12

Antibacterial Efficacy for Treatment of Halitosis

Campylobacter rectus, Helicobacter pylori, and Treponema denticola have been demonstrated to be associated with Halitosis (bad breath). The compounds and methods of the present invention, including CBS as well as ascorbyl bismuth derivative, have demonstrated in vitro activity against all three bacteria, as indicated by their minimum effective concentrations (MICs) presented in Table 12 below.

TABLE 12

| Test Organisms | Bismuth Ascorbyl Sulfate ($\mu$g/mL) | Bismuth Sucrose Sulfate ($\mu$g/mL) | CBS ($\mu$g/mL) |
|---|---|---|---|
| Campylobacter rectus | 256 | >256 | 256 |
| Helicobacter pylori | 8 | 16 | 2 |
| Treponema denticola | 16 | 32 | 32 |

EXAMPLE 13

In Vitro Mesentery Culture Model

Colloidal bismuth subcitrate and other bismuth compounds are known to accelerate wound healing by increasing the concentration of epithelial growth factor (EGF) and fibroblast growth factor (FGF) in the wounded tissue.

Utilizing a rat mesentery culture model (Wu et al., Annals of Plastic Surgery 33(2):155–161 (1994), incorporated herein by reference) and a medium containing 2% fetal calf serum, wound closure rates are measured. This tissue culture model is useful for gaining insights into growth factor interactions and wound healing. CBS or bismuth ascorbyl sulfate or glucose (placebo) are added to the medium in concentration ranges from 10 mcg/mL to 1,000 mcg/mL, and the wound closure is assessed at 24-hour, 48-hour and 72-hour intervals. Significantly higher concentrations of growth factors EGF and FGF are observed. Moreover, a significantly faster wound closure rate and complete closure is seen in the culture to which CBS or bismuth ascorbyl sulfate are added, compared to the placebo.

EXAMPLE 14

Diabetic Mouse Wound Healing Model

Further, wound healing potential of the above bismuth compounds is evaluated using a diabetic mouse wound healing model (Matuszewska et al., Pharmaceutical Research 11(1):65–71 (1994), incorporated herein by reference). Wounds treated with CBS and bismuth ascorbyl sulfate formulations at concentration ranges of 10 mcg/mL to 1,000 mcg/mL heal faster compared to placebo treated wound. The wound healing rates produced by the bismuth compounds are comparable to the wound healing rate produced by 0.5 to 5 mcg/mL concentration of basic fibroblast growth factor (bFGF).

EXAMPLE 15

Freeze-injured Skin Graft Model

The efficacy of CBS and bismuth ascorbyl sulfate at enhancing wound healing is also studied in a freeze-injured skin graft model for quantitative evaluation of promoters of wound healing (Lees et al., British Journal of Plastic Surgery 47(5):349–359 (1994), incorporated herein by reference). Application of CBS or bismuth ascorbyl sulfate stimulates wound healing in cryoinjured grafts in a dose-related fashion. Doses of 10 to 1000 mcg/mL produce significant increase in wound healing rates compared to placebo.

Topical dosage forms for wound healing will depend on whether corneal or dermal wound healing is sought. For dermal wound healing, occlusive or non-occlusive barriers can be used to achieve a pharmacologically desirable concentration over a desirable duration (i.e., sustained release). For corneal wound healing, it is desirable to release the dosage of bismuth compound over a period of at least 30 minutes, more preferably at least 1 hour, more preferably at least 6 hours, more preferably at least 12 hours, more preferably at least 24 hours, more preferably at least 36 hours, more preferably at least 48 hours, more preferably at least 60 hours, more preferably at least 72 hours. For both dermal and corneal treatment, the release of bismuth compounds should provide a concentration of at least 10 $\mu$g/mL, more preferably at least 100 $\mu$g/mL, more preferably at least 500 $\mu$g/mL, more preferably at least 1 mg/mL, more preferably at least 10 mg/mL, more preferably at least 100 mg/mL.

Dermal wound healing as disclosed herein also contemplates the treatment of acne vulgaris to eliminate bacteria and to repair epithelial cell damage. For this use, the topical dosage form should be able to penetrate the acne comedone (i.e., pustule having crusty surface), should permit comfortable application, and should not cause irritation of acne. As disclosed herein, suitable dosage forms include creams, gels, ointments, suspensions, etc., and will provide therapeutic concentrations as set forth above.

Thus, while several embodiments have been shown and described, various modifications may be made, without departing from the spirit and scope of the present invention.

What is claimed is:

1. A method of stimulating cellular production or release of growth factors, comprising administering to dermal cells of a wound a preparation comprising a bismuth compound in a topical dosage form, the bismuth compound being selected from the group consisting of colloidal bismuth subcitrate, bismuth subcitrate, bismuth citrate, bismuth salicylate, bismuth subsalicylate, bismuth subcarbonate, bismuth tartrate, bismuth subgallate, tripotassium dicitrato bismuthate, bismuth aluminate, bismuth polysulfates, bismuth polyhydroxy compounds, bismuth ascorbyl sulfate, bismuth subascorbate, bismuth cyclodextrin sulfate, and combinations thereof to stimulate said cellular production or release of growth factors.

2. The method of claim 1, wherein said topical dosage form is selected from the group consisting of ointments, gels, creams, solutions, suspensions, emulsions, dressings, and aerosols.

3. The method of claim 1, wherein the bismuth compound is applied in an occlusive barrier to promote wound healing.

4. The method of claim 1, wherein the bismuth compound is applied in a non-occlusive barrier to allow wound drainage.

5. The method of claim 1, wherein the step of administering a bismuth compound in a topical dosage form includes the step of delivering said bismuth compound to an area of diaper rash.

6. The method of claim 1, wherein the step of administering to dermal cells includes administration to acne to reduce or eliminate acne vulgaris.

7. The method of claim 1 wherein said bismuth compound is selected from the group consisting of alpha-D-glucopyranoside bismuth complex, beta-D-fructofuranosyl-octakis (hydrogen sulfate) bismuth complex, L-dihydro ascorbyl-tetrakis (hydrogen sulfate) bismuth complex, and combinations thereof.

8. A method of stimulating cellular production or release of growth factors, comprising the step of administering to corneal cells in an eye in need thereof a preparation comprising a bismuth compound in a topical dosage form to stimulate said cellular production or release of growth factors.

9. The method of claim 8, wherein said bismuth compound is selected from the group consisting of colloidal bismuth subcitrate, bismuth subcitrate, bismuth citrate, bismuth salicylate, bismuth subsalicylate, bismuth subnitrate, bismuth subcarbonate, bismuth tartrate, bismuth subgallate, tripotassium dicitrato bismuthate, bismuth aluminate, bismuth polysulfates, bismuth polyhydroxy compounds, bismuth ascorbyl sulfate, bismuth subascorbate, and bismuth cyclodextrin sulfate.

10. The method of claim 8, wherein said topical dosage form is selected from the group consisting of ointments, gels, creams, solutions, suspensions, emulsions, dressings, erodible and non-erodible inserts, and aerosols.

11. The method of claim 8, wherein said topical dosage form provides sustained release of bismuth compound in the eye to promote wound healing.

12. The method of claim 8, wherein said topical dosage form is a polymeric insert from which the bismuth compound is released over a 30-minute to 72-hour period.

13. The method of claim 8, wherein said topical dosage form is a soft contact lens impregnated with a bismuth compound to provide release over a 30-minute to 72-hour period.

14. The method of claim 8, wherein said bismuth compound is selected from the group consisting of alpha-D-glucopyranoside bismuth complex, beta-D-fructofuranosyl-octakis (hydrogen sulfate) bismuth complex, L-dihydro ascorbyl-tetrakis (hydrogen sulfate) bismuth complex, and combinations thereof.

15. The method of claim 10, wherein said topical dosage form comprises contact lenses.

* * * * *